(12) United States Patent
Kazem-Moussavi et al.

(10) Patent No.: US 10,004,452 B2
(45) Date of Patent: Jun. 26, 2018

(54) SYSTEM AND METHODS FOR ESTIMATING RESPIRATORY AIRFLOW

(75) Inventors: Zahra Kazem-Moussavi, Winnipeg (CA); Azadeh Yadollahi, Torronto (CA)

(73) Assignee: University of Manitoba, Winnipeg (CA)

( * ) Notice: Subject to any disclaimer, the term of this patent is extended or adjusted under 35 U.S.C. 154(b) by 158 days.

(21) Appl. No.: 14/342,010

(22) PCT Filed: Sep. 7, 2012

(86) PCT No.: PCT/CA2012/050621
§ 371 (c)(1),
(2), (4) Date: Jul. 7, 2014

(87) PCT Pub. No.: WO2013/033845
PCT Pub. Date: Mar. 14, 2013

(65) Prior Publication Data
US 2014/0330095 A1 Nov. 6, 2014

Related U.S. Application Data

(60) Provisional application No. 61/531,772, filed on Sep. 7, 2011.

(51) Int. Cl.
*A61B 5/00* (2006.01)
*A61B 7/00* (2006.01)
(Continued)

(52) U.S. Cl.
CPC ............ *A61B 5/4818* (2013.01); *A61B 5/087* (2013.01); *A61B 5/14542* (2013.01);
(Continued)

(58) Field of Classification Search
CPC ... A61B 5/4818; A61B 5/14542; A61B 5/087; A61B 5/7282; A61B 5/742; A61B 7/003; A61B 7/04
(Continued)

(56) References Cited

U.S. PATENT DOCUMENTS 4,802,485 A * 2/1989 Bowers ................ A61B 5/0816
600/324
5,522,382 A * 6/1996 Sullivan ................ A61B 5/097
128/204.21
(Continued)

FOREIGN PATENT DOCUMENTS

WO 2009036327 A1 3/2009

OTHER PUBLICATIONS

Yadollahi et al. "Acoustic Obstructive sleep apnea detection" 31st Annual International Conference of the IEEE EMBS Minneapolis, Minnesota, USA, Sep. 2-6, 2009.*
(Continued)

Primary Examiner — Nathan J Jenness
(74) Attorney, Agent, or Firm — Valauskas Corder LLC

(57) ABSTRACT

A system and methods for screening patients suspected of obstructive sleep apnea. The system includes a sound detection device configured for detecting tracheal respiratory sound signals of a patient and a Sao$_2$ detection device for detecting SaO2 signals of the patient. The system also has a head position detection device for detecting the head positions of the patient during testing, and a processing module for receiving and analyzing the tracheal respiratory sound signals to extract sound data and the Sao$_2$ signals to extract blood oxygen saturation data. The processing module further receives and analyzes the head position signals captured by the head position detection device to generate head position data. The system may further include a display for
(Continued)

displaying information about the various data generated by the processing module.

17 Claims, 3 Drawing Sheets

(51) Int. Cl.
*A61B 5/087* (2006.01)
*A61B 5/145* (2006.01)
*A61B 7/04* (2006.01)
*A61B 5/11* (2006.01)

(52) U.S. Cl.
CPC .......... *A61B 5/6823* (2013.01); *A61B 5/7282* (2013.01); *A61B 5/742* (2013.01); *A61B 7/003* (2013.01); *A61B 7/04* (2013.01); *A61B 5/1114* (2013.01)

(58) Field of Classification Search
USPC .................................................. 600/300, 301
See application file for complete search history.

(56) References Cited

U.S. PATENT DOCUMENTS 6,139,505 A * 10/2000 Murphy ................ A61B 5/061
 381/67
7,942,824 B1 5/2011 Kayyali et al.
2002/0165462 A1* 11/2002 Westbrook ........... A61B 5/0205
 600/529
2008/0243017 A1* 10/2008 Moussavi .............. A61B 5/087
 600/532
2012/0071741 A1 3/2012 Moussavi et al.

OTHER PUBLICATIONS

Yadollahi et al. "The Effect of Anthropometric Variations on Acoustical Flow Estimation: Proposing a Novel Approach for Flow Estimation Without the Need for Individual Calibration" IEEE Transactions on Biomedical Engineering, vol. 58, No. 6, Jun. 2011.*
Salles et al. "Obstructive sleep apnea and hypopnea syndrome: cephalometric analysis" Rev Bras Otorrinolaringol. V.71, n.3, 369-72, May/Jun. 2005.*
Yahollahi et al. ("A Robust Method for Estimating Respiratory Flow Using Tracheal Sounds Entropy IEEE Transactions on Biomedical Engineering, vol. 53, No. 4, Apr. 2006").*
Yadollahi, A. et al, "The effect of anthropometric variations on acoustical flow estimation: proposing a novel approach for flow estimation without the need for individual calibration", IEEE Transactions on Biomedical Engineering, vol. 58, No. 6, Jun. 2011 URL: <http://ieeexplore.ieee.org/stamp/stamp.jsp?tp~ &arnumber5705565>.

* cited by examiner

SYSTEM AND METHODS FOR ESTIMATING RESPIRATORY AIRFLOW

CROSS-REFERENCE TO RELATED APPLICATIONS

This application claims priority to U.S. Provisional Application No. 61/531,772, filed Sep. 7, 2011, which is incorporated by reference in its entirety.

STATEMENT REGARDING FEDERALLY SPONSORED RESEARCH OR DEVELOPMENT

Not applicable.

FIELD OF THE INVENTION

The invention relates generally to a system and methods of detecting events while a patient sleeps. More particularly, the present invention relates to a system and methods for calculating a relative estimation of respiratory airflow, detecting apnea events and hypopnea events while the patient is asleep, and also apnea/hypopnea index (AHI) and snoring events in different head/neck positions with respect to a torso of the patient.

BACKGROUND OF THE INVENTION

Sleep apnea is a sleep disorder characterized by pauses in breathing during sleep. By definition, sleep apnea is the cessation of airflow to the lungs during sleep which lasts for at least 10 seconds, and is usually associated with more than a 4% drop in blood oxygen saturation ("$SaO_2$") level. There are three distinct forms of sleep apnea: central; obstructive; and complex. Complex sleep apnea is defined as a combination of central and obstructive sleep apnea. It is estimated that central, obstructive, and complex sleep apnea account for approximately 0.4%, 84% and 15% of the reported cases, respectively. With central sleep apnea, a patient's breathing is interrupted by the lack of respiratory effort. With obstructive sleep apnea, partial or complete collapse of airways interrupts patient breathing. With complex sleep apnea, there is a transition by a patient from central sleep apnea characteristics to obstructive sleep apnea characteristics during breathing.

Obstructive sleep apnea ("OSA") is the most common respiratory disorder that may lead to a myriad of problems including daytime fatigue, irritability, impaired concentration, poor job performance, increased risk of accidents, and cardiovascular problems. OSA is most common in people with high blood pressure, people with a narrowed airway due to tonsils or adenoids, and people who smoke tobacco products. OSA occurs more frequently in elderly, and is more common among males than females.

Currently, polysomnography ("PSG") is a preferred tool for diagnosing sleep apnea. PSG includes a comprehensive recording of biophysiological changes in a patient during sleep. A typical PSG test includes recording various biological signals, including brain signals ("EEG"), heart rhythm signals ("ECG"), muscle activity or skeletal muscle activation signals ("EMG") of chin and legs, nasal airflow signals, electro-oculogram or eye movement signals ("EOG"), and abdominal and thoracic movement signals. A disadvantage of PSG time gathering and evaluating the biological signals is time consuming. Further, PSG is inconvenient and expensive because it requires a full night of patient supervision by a healthcare professional.

Alternative technologies for diagnosing sleep apnea may record a reduced number of signals and detect apnea events during sleep. Many of the current technologies record patient airflow. In these technologies, patient breathing airflow may be measured by either a face mask or a nasal cannula connected to a pressure transducer, and cessation of patient breathing airflow is detected as the main diagnostic sign of sleep apnea, particularly OSA. In the case of mouth breathing by a patient, which may occur often during the night, the nasal cannula will not register airflow. Therefore, a nasal cannula is not very reliable. On the other hand, using a face mask, which is considered a more reliable device for breathing airflow measurement, may change the breathing pattern of the patient. Additionally, it is difficult for some patients to fall asleep wearing a face mask.

A majority of people (~70%) who undergo a full-night sleep study are not diagnosed as severely apneic. Therefore, there is a need for a non-invasive system and methods to pre-screen patients suspected of sleep apnea that avoids the inconveniences of current invasive respiratory airflow detection devices such as nasal cannulae and masks. The present invention satisfies this demand.

SUMMARY OF THE INVENTION

The present invention is a system and methods to gather data about patients to diagnose patients for OSA. The system and methods are non-invasive and provide patient screening results that are comparable in accuracy to tests using full-night PSG. An acoustical analysis is conducted on the tracheal respiratory sound signals of the patient to extract characteristics of a patient's breathing. A probe measures the $SaO_2$ signals of a patient, and head sleep positions are detected.

Patients with some degree of upper airway congestion are more prone to develop OSA. Patients with OSA commonly have a defective ability to dilate the airways during inspiration. The classification of patients with OSA is determined by an apnea/hypopnea index ("AHI") which shows the number of apnea and hypopnea events per hour: AHI<5 classifies patients as non-OSA, 5<AHI<15 classifies patients as mild, 15<AHI<30 classifies patients as moderate, and AHI>30 classifies patients as severe.

As used herein, an "apnea event" is defined as cessation of airflow signal lasting 10 seconds or longer followed by a decrease in $SaO_2$. By "cessation of airflow" is meant a reduction of more than 90% in the amplitude of respiratory airflow from its baseline. A "hypopnea event" as used herein refers to a reduction in airflow signal to less than 50% of its baseline amplitude, accompanied by a ≥3% reduction in $S_aO_2$ In one embodiment of the invention, a non-invasive system for screening a patient for OSA includes a sound detection device configured for detecting tracheal respiratory sound signals of a patient. The system also includes a $SaO_2$ detection device and a head position detection device for detecting the head positions of the patient under test. In one embodiment, the $SaO_2$ detection device is a pulse oximetry device for detecting $SaO_2$ signals of the patient. Additionally, the system includes a processing module for receiving and analyzing the patient tracheal respiratory sound signals and $SaO_2$ signals to extract breathing data. The processing module further receives and analyzes the head position data captured by the head position detection device. The system may also include a display for displaying information about the various data received by the processing module.

In one embodiment, the sound detection device is a microphone configured to be located on a patient's neck over the patient's suprasternal notch for detecting the tracheal sounds of the patient.

In some embodiments, the $SaO_2$ detection device is a finger probe that detects $SaO_2$ signals of a patient.

In one embodiment, the head position detection device is an accelerometer placed on a patient's head, e.g., on the patient's forehead, for detection of the head position of the patient.

In certain embodiments, the processing module is configured for receiving and analyzing the tracheal respiratory sound signals and $SaO_2$ signals from a patient to extract data related to the breathing of the patient and apnea and hypopnea events.

In one embodiment, the processing module analyzes the tracheal respiratory sound signals and $SaO_2$ signals of a patient to generate an estimate of airflow while extracting snoring sounds and heart sounds from the recorded tracheal sounds of the patient. Respiratory airflow is calculated based on the energy of tracheal sound. The relationship between respiratory air flow and sound follows a power law, which may be expressed as $A_s = kF^\alpha$ where $E_s$ and F represent the tracheal sound's average power and flow, respectively. Therefore, a linear relationship exists between the air flow and sound's average power in logarithm scale loci F=a loci $E_s$+b where a=1/α and b=−log k/α. The sound's average power $E_s$ may be estimated by calculating the signal's variance, where the logarithm of the sound's variance follows the changes in the breathing flow. Such a method was applied and tested on data of different individuals during wakefulness and sleep (Yadollahi and Moussavi, IEEE Trans Biomed Eng 2011 58(6) 1663-1670); Yadollahi et al. Respiratory Flow-Sound relationship during Wakefulness and Sleep and its Variation in Relation to Sleep Apnea, *Ann Biomed Eng.* 2013 41(3) 537-46) using the following model equation:

$$\log F_{est} = E_s/E_{base} \times á \log E_s + b́ = E_s \times [á/E_{base}] \times \log E_s + b́,$$

where $F_{est}$ is the estimated respiratory flow, $E_s$ is the tracheal sound energy. The model parameters á and b́—which relate to the power of the tracheal respiratory sound signals and the variations in tracheal anatomy producing the tracheal respiratory sound signals, respectively—may be derived through a calibration process for every subject. However the rate of increase in sound's energy is not similar at different respiratory flow rates. Therefore, using the same parameters á and b́ for all respiratory flow rates will cause over/under estimation at the lower/higher respiratory flow rates than the flow rate used for calibrating the model (M. Golabbakhsh, "Tracheal breath sound relationship with respiratory flow: Modeling, the effect of age and airflow estimation," Master's thesis, Electrical and Computer Engineering Department, University of Manitoba, 2004; I. Hossain and Z. Moussavi, "Respiratory airflow estimation by acoustical means," in Proc. Second joint EMBS/BMES Conf., Houston, Tex., USA, 2002, pp. 1476-1477), and where $\bar{E}$ is the average of sound's energy, $E_s$ is the sound's energy in the overlapping windows of current breath cycle, and $E_{base}$ is the sound's energy in the breath cycle used for calibrating the model equation.

Since the sound generation mechanisms are different during inspiration and expiration, different parameters may be extracted for each phase. Hence, $a_{ins}$, $b_{ins}$, $a_{exp}$, and $b_{exp}$ represent the model parameters during inspiration and expiration phases, respectively, where $a_{ins} = á/E_{base-ins}$ and $a_{exp} = á/E_{base-exp}$ are normalized values of a-parameter during inspiration and expiration, respectively. This normalization also cancels out the effects of sound variations between individuals.

Multiple approaches, using, for example, linear regression based on a least mean squared error, may be used to calibrate the model equation, and estimate parameters á and b́. In the one approach, the subject's data, including the recorded tracheal sound and respiratory airflow by using, for example, a microphone or other audio recorder and pneumotachograph connected to a differential pressure transducer, respectively, during wakefulness to calibrate the model and estimate respiratory air flow and tracheal sound during sleep. Therefore, the model equations may be calibrated using one breath cycle with known respiratory flow recorded during wakefulness at a similar head position to the data during sleep. In another approach, one breath cycle with known respiratory flow during sleep may be used to calibrate the model and estimate parameters á and b́. To compare different calibration schemes, the changes in model parameters may be investigated from wakefulness to sleep, and the respiratory flow estimation error using different calibration approaches may be estimated according to the following:

$$\text{Error} = \frac{\text{mean}(F - Fest)^2}{\text{mean}(F^2)} \times 100.$$

In some embodiments, the processing module is configured to estimate the air volume in the respiratory phases adjacent to the snoring phases in order to remove the effects of snoring sounds on the tracheal sounds and have an estimate of respiratory air volume of the patient in the respiratory phases including snoring sounds.

In one embodiment, the processing module is configured for presenting an estimated respiratory airflow to monitor a breathing pattern of a patient during a time period. The time period may be any duration, such as throughout the time a patient sleeps at night.

In certain embodiments, the processing module is configured for analyzing the estimated respiratory airflow to detect time periods of apnea and/or hypopnea events experienced by the patient under testing.

In one embodiment, the processing module is configured for analyzing the head position detection device data to detect the head position of a patient during the night.

In one embodiment, the processing module is configured for using the detected snoring sounds of a patient to estimate a severity of snoring sounds and a duration of snoring sounds based on an energy and the frequency response of the detected snoring sounds.

In one embodiment, the processing module is configured for using the head position detection device data and detected apnea events and detected hypopnea events to determine the number of apnea events and hypopnea events at different head positions.

In one embodiment, the processing module is configured for using the snoring information and head position information of a patient and report the severity and duration of snoring in every head position.

In one embodiment, the system includes a display showing the detected apnea events and hypopnea events, snoring severity at every head position along with the related information about a patient. In certain embodiments, a display of the relative respiratory airflow and snoring of a patient for the entire night with zoom in and out options, a display of the recorded respiratory air signals, and snoring sounds and head position of the patient with zoom in and out options with the pathological events highlighted in a red color are provided.

In some embodiments, the processing module may connect to an interface for transmission of data to different locations.

In one embodiment, the display has airflow versus time plotted with apnea events and hypopnea events marked in the display.

In some embodiments, the display has snoring severity versus time plotted, snoring severity versus head position plotted, snoring duration versus time of sleep plotted, and snoring duration versus head position plotted for a patient. The display may also include oximetry data plotted in association with the estimated respiratory airflow for a patient.

In some embodiments, the display provides a display of apnea events and hypopnea events versus head positions for one or more patients.

In some embodiments, the display includes snoring severity and duration in association with the head position. The display may be capable of zoom-in and zoom-out functions in the same window for airflow, snoring and oximetry data simultaneously for a patient.

In some embodiments, the display is capable of playing the breathing sounds, snoring sounds, and displaying monitored head positions in any zoomed-in or zoomed-out sub-window provided on the display for a patient.

In some embodiments, the display is capable of displaying the extracted information about the frequency and duration of apnea events and hypopnea events, and the association of the apnea events and the hypopnea events with the level of oximetry data in a separate window for a patient.

In some embodiments, the display is capable of displaying the extracted information about the frequency and duration of apnea events and hypopnea events, and the association of the apnea events and hypopnea events with the head position of a patient in a separate window for a clinician to review.

In yet another embodiment, the display is capable of displaying extracted information about the severity and duration of snoring sounds, and the snoring sounds association with the head position of a patient in a separate window for a clinician to review.

In some embodiments of the system, the sound detection device and/or the head detection device may be wireless.

In some embodiments, the system includes an additional sound detection device such as a microphone attached to the chest of a patient to collect lung sound signals from the patient.

In another embodiment of the invention, a method for analysis of breathing airflow of a patient during sleep includes detecting tracheal respiratory sound signals of the patient by a sound detection device located on the neck of the patient and monitoring detected head position signals from a head position detection device to detect head positions of a patient. The method includes examining blood oxygen saturation of a patient for recording a blood oxygen saturation signal, and receiving and analyzing the tracheal respiratory sound signals in a processing module to generate airflow data corresponding to airflow of the patient during breathing cycles.

The method includes collecting and processing the tracheal respiratory sound signals in the processing module to generate snoring data corresponding to snoring characteristics of the patient. The method also includes obtaining and examining the detected head position signals at the processing module to generate head position data. The method further includes evaluating the blood oxygen saturation signal to detect any changes in the blood oxygen saturation of the patient. Upon detection of a drop of the blood oxygen saturation of a patient that is greater than a predetermined level, the method may include ignoring during the drop of the blood oxygen saturation at least some of the tracheal respiratory sound signals when generating the airflow data.

In one embodiment, the method may have the sound signals used for calculating an index of snoring severity and duration of the patient.

In one embodiment, the method may provide a display for displaying an estimated patient respiratory airflow relative to time of the patient.

In one embodiment, the method may have a display arranged to show the estimated patient respiratory airflow versus time in any desired time length being chosen by a user of the display.

In one embodiment, the method may have a display that is capable of zoom-in and zoom-out functions in the same window shown on the display.

In one embodiment, the method may have a display that is capable of playing the captured breathing sounds of the patient in any data window.

In one embodiment, the method may have a display for displaying the detected snoring of the patient relative to the head position of the patient.

In one embodiment, the method may have a display arranged to display the detected snoring of a patient versus head position of a patient in any desired time length being chosen by a user of the display.

In one embodiment, the method may have a display capable of zoom-in and zoom-out functions in the same window shown on the display.

In one embodiment, the method may have a display capable of playing the snoring sounds of the patient in any data window shown on the display.

In one embodiment, the method may have a processing module arranged to calculate a function representing a range of a sound signal or entropy of the sound signal to provide an estimate of respiratory airflow of the patient during breathing cycles.

In one embodiment, the method may have a processing module arranged to calculate a function, wherein the function is the range of a sound signal which is defined as the log of the difference between minimum and maximum amplitudes of the sound signal within each predetermined short window of data.

In one embodiment, the method may have a processing module arranged to calculate a function using entropy which is defined by the following formula.

$$H(p) = -\sum_{i=1}^{N} p_i \log p_i,$$

where $p_i$ is the probability distribution function of the $i^{th}$ event, p is the probability distribution function of the tracheal sound amplitude. P is defined in N bins, which span the range of values from minimum of tracheal sound amplitude to the maximum of tracheal sound amplitude. Pi is the number of tracheal sound samples with values equal to its bin divided by total number of tracheal sound samples.

In one embodiment, the sound detection device is a microphone located in the ear of a patient.

In one embodiment, the method may have inspiration and expiration of a patient monitored by a smart program module which detects respiratory phases based on a relationship between sound duration and sound energy of successive breathing cycles.

In one embodiment, the method may have a processing module to calculate an estimate of respiratory airflow rate of a patient that is calibrated using a look-up table of previously measured airflow-sound relationship data which is sorted based on characteristics of patients. In certain embodiments, the characteristics in the look-up table may include ethnicity, body mass index ("BMI"), gender, height, neck circumference, and smoking history of the patient.

An alternative embodiment of a method for analysis of breathing airflow of a patient during sleep includes detecting tracheal respiratory sound signals of the patient by a sound detection device located on or near the patient to generate sound data, receiving and evaluating the sound signals to generate airflow data relating to airflow of the patient during breathing cycles, and analyzing the sound signals to detect snoring of the patient.

The method further includes upon detection of snoring of the patient, ignoring during the snoring breathing cycle at least some of the sound signals in generating the sound data. The method may further generate information about the breathing airflow of the patient. In some embodiments, the information about the breathing airflow of the patient may be displayed on a display.

In one embodiment, the method may use a sound detector that measures the sound segments energy in decibels, the number of zero crossing rate ("ZCR") of the sound signals in each 20 ms window of data that is captured, and the first formant frequency of the sound signals to classify the sound segments into two groups of breath group and snore group.

In one embodiment, the method may utilize a Fisher Linear Discriminant ("FLD") module to transform the sound segments energy, ZCR, and first formant frequency into a new one-dimensional space and then minimize the Bayesian error to classify the sound segments as breath sound segments or snore sound segments.

In one embodiment, the method may process the snoring of a patient which occurs in only one of two successive respiratory phases of inhale and exhale. Sound signals from the other respiratory phase are used to estimate airflow of the patient in both of the two successive respiratory phases by deciding that the amount of inhaled air is equal to the amount of exhaled air of the patient.

In one embodiment, the method uses the sound signals for calculating an index of apnea events and hypopnea events.

In one embodiment, the method provides analysis of accelerometer signals generated by an accelerometer positioned on the patient's forehead to detect the head positions of a patient in a sagittal plane and a coronal plane.

In one embodiment, the method may provide a display for displaying an estimated airflow of a patient relative to time. In certain embodiments, the estimated airflow of the patient versus time may be displayed in any desired time length being chosen by a user of the display.

In one embodiment, the display is capable of zoom-in and zoom-out functions in the same window of the display. Moreover, in certain embodiments the display is capable of playing the sound signals of a patient in any data window shown on the display.

In one embodiment, the method may provide a display for displaying detected snoring sounds of a patient relative to time. In some embodiments, the display is arranged to display the detected snoring of the patient versus time in any desired time length chosen by a user of the display.

In some embodiments, the display is capable of zoom-in and zoom-out functions in the same window of the display and/or playing the snoring sounds of a patient in any data window of the display.

In one embodiment, the method may have a processing module arranged to detect an index of apnea events and hypopnea events.

In one embodiment, the method may provide a display for a display of duration and frequency of apnea and hypopnea events versus head position of the patient.

In one embodiment, the method may provide a display to display the duration and frequency of apnea and hypopnea events in any desired time length and/or head position of the patient being chosen by a user of the display.

In one embodiment, the method may provide a display that is capable of zoom-in and zoom-out functions in the same window shown on the display.

In one embodiment, the method may have a processing module arranged to estimate severity and duration of snoring sounds of a patient. Severity of snoring sounds may be estimated based on the sound energy and sound frequency components of snoring sounds of a patient.

In one embodiment, the method may provide a display to display duration and severity of snoring sounds versus head position of a patient.

In one embodiment, the method may provide a display to display the duration and severity of snoring sounds in any desired time length and/or head position of a patient that is chosen by a user of the display.

In one embodiment, the method may provide a display capable of zoom-in and zoom-out functions in the same window of the display.

The present invention and its attributes and advantages will be further understood and appreciated with reference to the detailed description below of presently contemplated embodiments, taken in conjunction with the accompanying drawings.

BRIEF DESCRIPTION OF THE DRAWINGS

The preferred embodiments of the invention will be described in conjunction with the appended drawings provided to illustrate and not to limit the invention, where like designations denote like elements, and in which.

DETAILED DESCRIPTION OF EMBODIMENTS OF THE INVENTION

Figure 1:
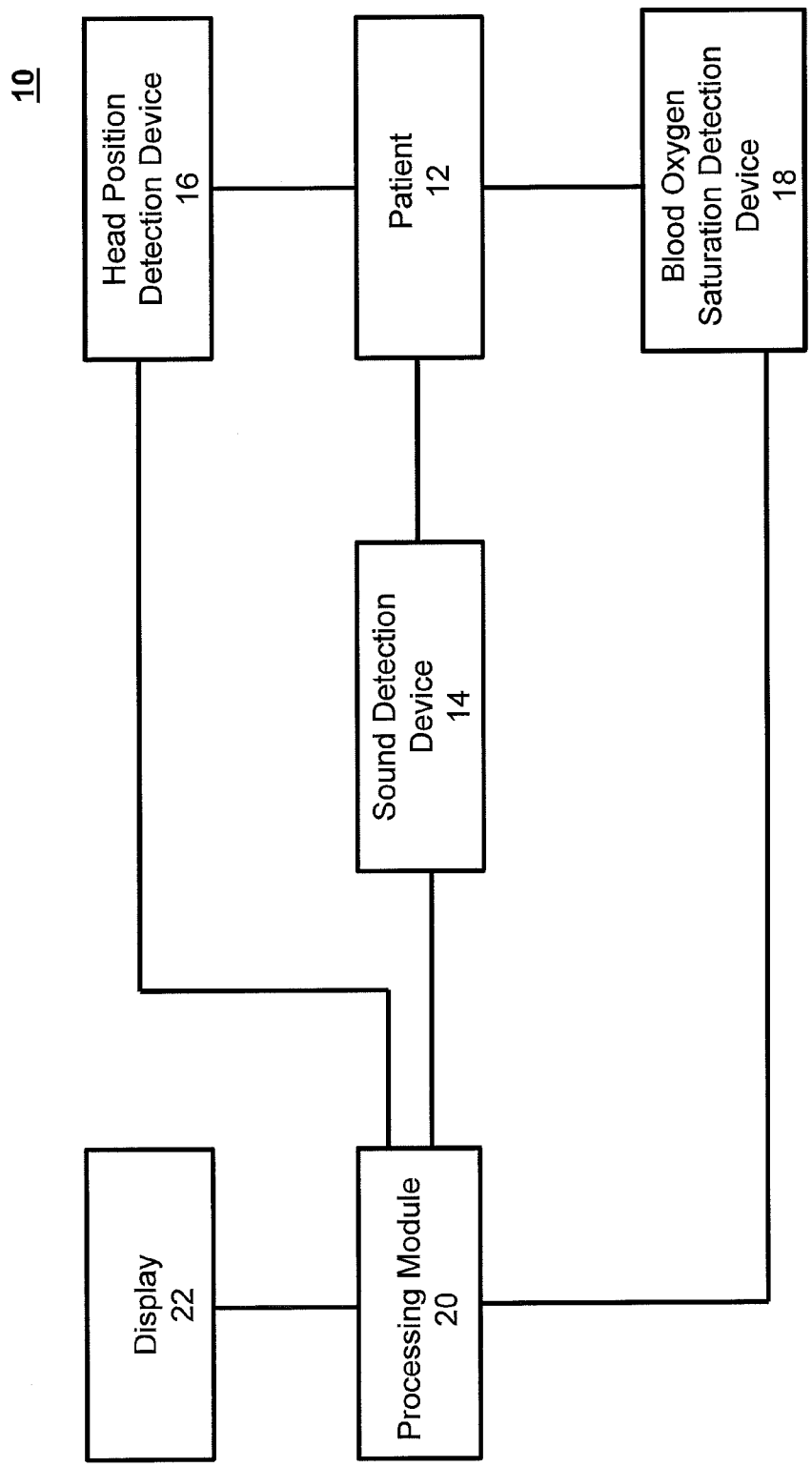
FIG. 1 is a block diagram of a system for analyzing respiratory airflow of a patient during sleep according to one embodiment of the present invention.

FIG. 1 illustrates a system 10 for analyzing airflow of a patient 12 during sleep according to one embodiment of the present invention. The system 10 includes a sound detection device 14 positioned on or near the patient 12. The sound detection device 14 may be one or more microphones or other devices that capture sounds of the patient 12. The sounds may be breathing sounds, heart sounds, lung sounds, etc. of a patient. A user of the system preferably positions the sound detection device 14 on the suprasternal notch of the trachea of the patient 12 while the patient 12 is sleeping.

The system 10 also includes a head position detection device 16. The head position detection device 16 determines the head position of the patient 12. In certain embodiments, an accelerometer may determine the head positions of a patient 12. The accelerometer may be placed on the forehead of the patient 12 while the patient is undergoing testing.

The system 10 further includes a blood oxygen saturation detection device 18. The blood oxygen saturation detection device 18 detects the blood oxygen saturation of the patient 12. In certain embodiments, the blood oxygen saturation of the patient 12 may be detected at set time periods or during each breathing cycle of the patient. In some embodiments, a finger probe may be as the blood oxygen saturation detection device 18. Moreover, any of the detection devices 14, 16, and 18 may be configured to perform a measurement on the patient 12 based on one of the other detection devices 14, 16, and 18 performing a measurement on the patient 12.

The detection devices 14, 16, and 18 provide inputs to a processing module 20 for further processing by the system 10. Processing module 20 is shown as a single entity, however it is envisioned that the processing module 20 can be formed of multiple modules. In some embodiments, the detection devices 14, 16, and 18 may have a wireless connection to the processing module 20.

The processing module 20 is configured to receive sound detection data for the sound detection device 14 and head position data from the head position detection device 16. The processing module 20 further receives blood oxygen saturation data from the blood oxygen saturation detection device 18. The various sound selection data, head position data, and blood oxygen saturation data are further processed by the processing module 20 to provide information to a user of the system 10.

In certain embodiments, the system 10 may include a display 22 which is connected to the processing module 20. The display 22 may be wirelessly connected to the processing module 20, and may be a smart phone, tablet, or any other hand-held computing device that is configured to display output from a computing device.

Figure 2:
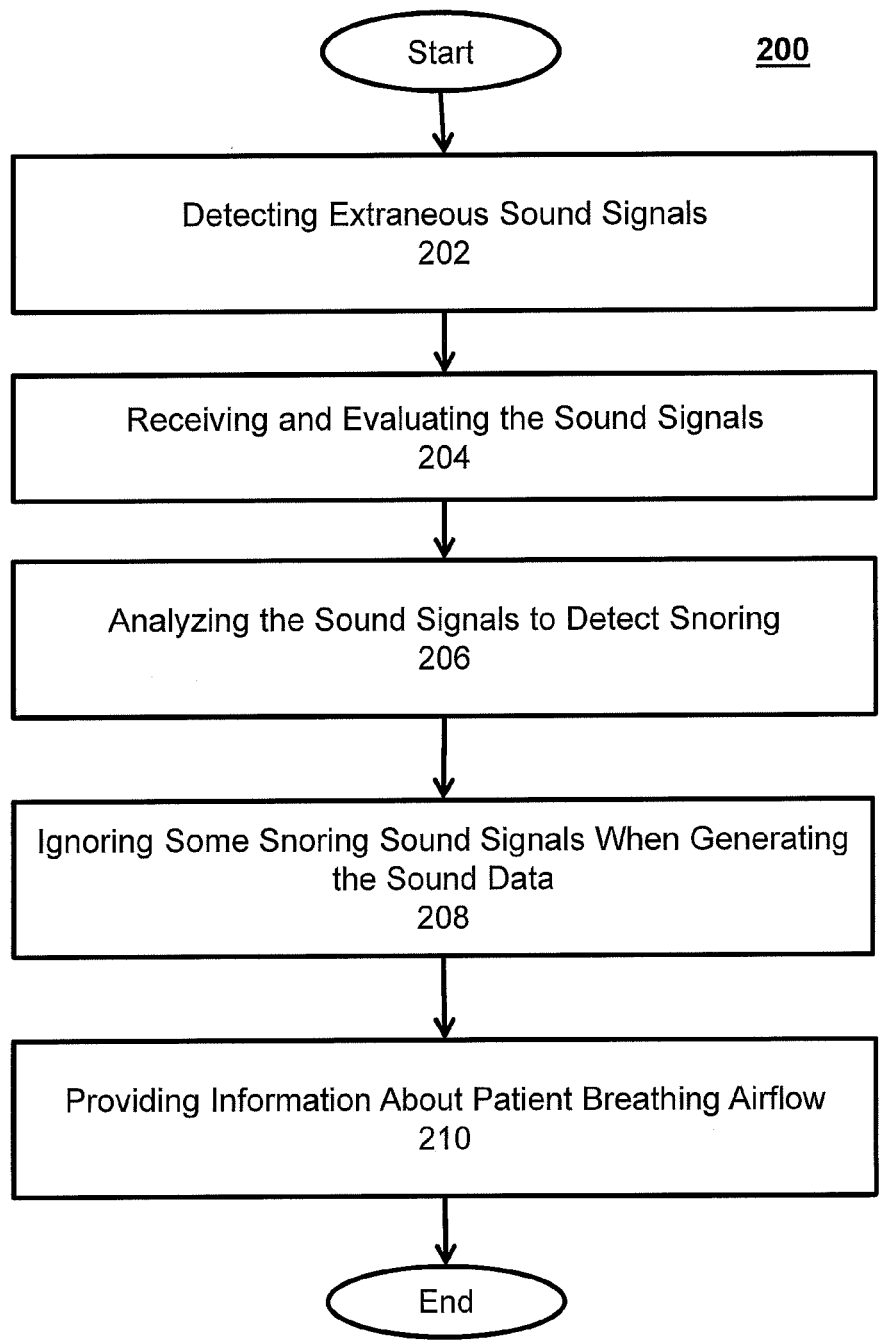
FIG. 2 is a flow chart illustrating a method for analyzing respiratory airflow of a patient according to one embodiment of the present invention.

FIG. 2 shows one embodiment of a method 200 for analysis of breathing airflow of a patient during sleep and includes detecting tracheal sound signals of the patient by a sound detection device located on or near the patient to generate sound data at step 202. Next, the method 200 has a step 204 of receiving and evaluating the sound signals to generate airflow data relating to airflow of the patient during breathing cycles. After step 204, the method 200 includes analyzing the sound signals to detect snoring of the patient at step 206. Upon detection of snoring of the patient, the method 200 includes ignoring during the snoring breathing cycle at least some of the sound signals when generating the sound data at step 208. The method 200 may provide information about the patient breathing airflow at step 210 and then end.

Figure 3:
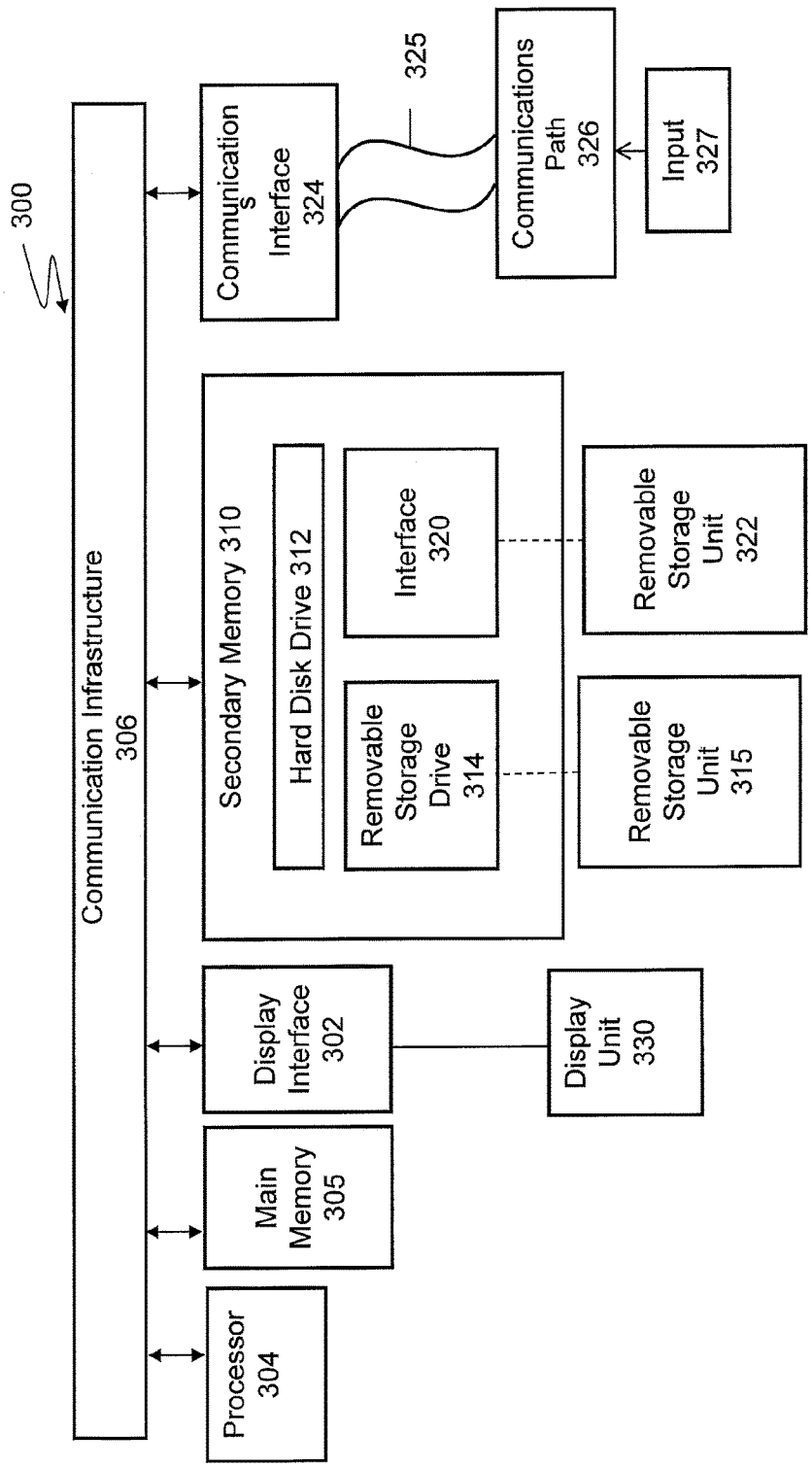
FIG. 3 is a schematic of a computer system for implementing the methods of the invention.

FIG. 3 illustrates an exemplary computer system 300, or network architecture, that may be used to implement the methods according to the present invention. One or more computer systems 300 may carry out the methods presented herein as computer code. One or more processors, such as processor 304, which may be a special purpose or a general-purpose digital signal processor, is connected to a communications infrastructure 306 such as a bus or network. Computer system 300 may further include a display interface 302, also connected to communications infrastructure 306, which forwards information such as graphics, text, and data, from the communication infrastructure 306 or from a frame buffer (not shown) to display unit 330. Computer system 300 also includes a main memory 305, for example random access memory ("RAM"), read-only memory ("ROM"), mass storage device, or any combination thereof. Computer system 300 may also include a secondary memory 310 such as a hard disk drive 312, a removable storage drive 314, an interface 320, or any combination thereof. Computer system 300 may also include a communications interface 324, for example, a modem, a network interface (such as an Ethernet card), a communications port, a PCMCIA slot and card, wired or wireless systems, etc.

It is contemplated that the main memory 305, secondary memory 310, communications interface 324, or a combination thereof function as a computer usable storage medium, otherwise referred to as a computer readable storage medium, to store and/or access computer software and/or instructions.

Removable storage drive 314 reads from and/or writes to a removable storage unit 315. Removable storage drive 314 and removable storage unit 315 may indicate, respectively, a floppy disk drive, magnetic tape drive, optical disk drive, and a floppy disk, magnetic tape, optical disk, to name a few.

In alternative embodiments, secondary memory 310 may include other similar means for allowing computer programs or other instructions to be loaded into the computer system 300, for example, an interface 320 and a removable storage unit 322. Removable storage unit 322 and interface 320 allows software and instructions to be transferred from the removable storage unit 322 to the computer system 300 such as a program cartridge and cartridge interface (such as that found in video game devices), a removable memory chip (such as an EPROM, or PROM) and associated socket, etc.

Communications interface 324 allows software and instructions to be transferred between the computer system 300 and external devices. Software and instructions transferred by the communications interface 324 are typically in the form of signals 325 which may be electronic, electromagnetic, optical or other signals capable of being received by the communications interface 324. Signals 325 are provided to communications interface 324 via a communications path 326. Communications path 326 carries signals 325 and may be implemented using wire or cable, fiber optics, a phone line, a cellular phone link, a Radio Frequency ("RF") link or other communications channels.

Computer programs, also known as computer control logic, are stored in main memory 305 and/or secondary memory 310. Computer programs may also be received via communications interface 324. Computer programs, when executed, enable the computer system 300, particularly the processor 304, to implement the methods according to the present invention. The methods according to the present invention may be implemented using software stored in a computer program product and loaded into the computer system 300 using removable storage drive 314, hard drive 312 or communications interface 324. The software and/or computer system 300 described herein may perform any one of, or any combination of, the steps of any of the methods presented herein. It is also contemplated that the methods according to the present invention may be performed automatically, or may be invoked by some form of manual intervention.

The sound detection device 14, head position detection device 16, and blood oxygen saturation detection device 18 may connect to the system 300 at the communications path 326 and provide input 327 to the system 300. However, it is envisioned that in other embodiments input 327 may be connected at other parts of the system 300 as is known to those skilled in the art.

The invention is also directed to computer products, otherwise referred to as computer program products, to provide software to the computer system 300. Computer products store software on any computer useable medium. Such software, when executed, implements the methods according to the present invention. Embodiments of the invention employ any computer useable medium, known now or in the future. Examples of computer useable mediums include, but are not limited to, primary storage devices (e.g., any type of random access memory), secondary storage devices (e.g., hard drives, floppy disks, CD ROMS, ZIP disks, tapes, magnetic storage devices, optical storage devices, Micro-Electro-Mechanical Systems ("MEMS"), nanotechnological storage device, etc.), and communication mediums (e.g., wired and wireless communications networks, local area networks, wide area networks, intranets, etc.). It is to be appreciated that the embodiments described herein may be implemented using software, hardware, firmware, or combinations thereof.

The computer system 300, or network architecture, of FIG. 3 is provided only for purposes of illustration, such that the present invention is not limited to this specific embodiment. It is appreciated that a person skilled in the relevant art knows how to program and implement the invention using any computer system or network architecture.

The described embodiments above are to be considered in all respects only as illustrative and not restrictive, and the scope of the invention is not limited to the foregoing description. Those of skill in the art will recognize changes, substitutions and other modifications that will nonetheless come within the scope of the invention and range of the claims.

Each cited reference is incorporated by reference in its entirety.

What is claimed is:

1. A system for analyzing breathing airflow of a patient during sleep, comprising:
    a sound detection device configured to be located adjacent a suprasternal notch of a trachea of the patient for detecting tracheal respiratory sound signals of the patient during a sleep event;
    a $SaO_2$ detection device for detecting $SaO_2$ signals of the patient;
    a head position detection device detecting head positions of the patient and generating head position data; and
    a processing module for receiving and analyzing both the tracheal respiratory sound signals and the $SaO_2$ signals, the processing module connected to the sound detection device, the $SaO_2$ detection device, and the head position detection device, the sound detection device measuring both a sound energy in decibels and a first formant frequency of each tracheal respiratory sound signal;
    a fisher linear discriminant module configured to transform both the sound energy and the first formant frequency of each tracheal respiratory signal into a one-dimensional space, the fisher linear discriminant module further minimizing a Bayesian error of the one-dimensional space to classify each tracheal respiratory sound signal as a breathing sound signal or a snoring sound signal;
    the processing module removing the snoring sound signals from the tracheal respiratory sound signals to produce filtered tracheal respiratory sound signals, and estimating a respiratory airflow rate of the filtered tracheal respiratory sound signals according to the following:

$$\log F_{est} = \overline{E}_s/\overline{E}_{base} \times \acute{a} \log E_s + \acute{b} = \overline{E}_s \times [\acute{a}/\overline{E}_{base}] \times \log E_s + \acute{b},$$

where $F_{est}$ is an estimated respiratory flow rate, $E_s$ is tracheal sound energy in overlapping windows of a breath cycle, á is a patient parameter representing power of the tracheal respiratory sound signals and b is a patient parameter representing variations in tracheal anatomy producing the tracheal respiratory sound signals, $\overline{E}$ is an average of the tracheal sound energy, and $E_{base}$ is tracheal sound energy in the breath cycle used for calibration, wherein the patient parameters are derived from at least one breath cycle of the patient;
    the processing module further configured to calculate an entropy of the filtered tracheal respiratory sound signals according to the following:

$$H(p) = -\Sigma_{i=1}^{n} p_i \log p_i$$

wherein H is a probability distribution function of a sleep event, p is a probability distribution function of a tracheal sound amplitude, wherein p is defined in n bins with each bin spanning a range of values from a minimum tracheal sound amplitude to maximum tracheal sound amplitude, $p_i$ is a number of tracheal sound samples with a value equal to the $i^{th}$ bins divided by a total number of tracheal sound samples in the sleep event; and
    the processing module using the estimated respiratory airflow rate and the entropy to determine apneas or hypopneas; and
    a display showing the estimated respiratory airflow rate.

2. The system according to claim 1, wherein the display illustrates a plot of the estimated respiratory airflow rate versus time.

3. The system according to claim 1, wherein the display illustrates the apneas or the hypopneas.

4. The system according to claim 3, wherein the display illustrates a plot of a number of the apneas and the hypopneas versus head position.

5. The system according to claim 1 the processing module extracting heart sounds from the tracheal respiratory sound signals of the patient.

6. The system according to claim 1, wherein the sound detection device is a microphone.

7. The system according to claim 1 further comprising an additional sound detection device configured to be attached to a chest of the patient for collecting lung sound signals of the patient.

8. The system according to claim 1, wherein the $SaO_2$ detection device is a finger probe.

9. The system according to claim 1, wherein the head position detection device is an accelerometer configured to be placed on the forehead of the patient.

10. The system according to claim 1, wherein the apneas are defined as a reduction of more than 90% in an amplitude of the respiratory airflow rate from a baseline followed by a decrease in the $SaO_2$ signals.

11. The system according to claim 1, wherein the hypopneas are defined as a reduction of more than 50% in an amplitude of the respiratory airflow rate from a baseline followed by decrease in the $SaO_2$ signals ≥3%.

12. The system according to claim 1, wherein the processing module determines a snoring sound energy and a snoring sound frequency from the removed snoring sound signal to estimate a severity of the snoring sound signal and a duration of the snoring sound signal.

13. The system according to claim 12 further comprising a head position detection device detecting head positions of the patient and the display illustrating one or more plots selected from the group comprising:

snoring severity versus time, snoring severity versus head position, snoring duration versus time, and snoring duration versus head position, both snoring severity and snoring duration versus time, both snoring severity and snoring duration versus head position.

14. A method for analyzing breathing airflow of a patient during sleep comprising:

placing a sound detection device for detecting tracheal respiratory sound signals of the patient during a sleeping event adjacent to the suprasternal notch of the patient;

measuring by the sound detection device both a sound energy in decibels and a first formant frequency of each tracheal respiratory sound signal;

attaching to the patient an $SaO_2$ detection device for detecting $SaO_2$ levels of the patient;

placing on the head of the patient a head position detection device for detecting head positions of the patient and generating head position data;

collecting and analyzing the tracheal respiratory sound signals, $SaO_2$ levels, and head position data using a processing module;

transforming by a fisher linear discriminant module both the sound energy in decibels and the first formant frequency of each tracheal respiratory sound signal into a one-dimensional space;

minimizing by the fisher linear discriminant module a Bayesian error of the one-dimensional space to classify each tracheal respiratory sound signal as a breathing sound signal or a snoring sound signal;

removing by the processing module the snoring sound signal to produce filtered tracheal respiratory sound signals;

determining by the processing module breathing data from the filtered tracheal respiratory sound signals comprising a respiratory airflow rate of the patient, wherein the respiratory airflow rate of the patient is defined as:

$$\log F_{est} = \overline{E}_s / \overline{E}_{base} \times \acute{a} \log E_s + \acute{b} = \overline{E}_s \times [\acute{a}/\overline{E}_{base}] \times \log E_s + \acute{b},$$

where $F_{est}$ is an estimated respiratory flow rate, $E_s$ is tracheal sound energy in overlapping windows of a breath cycle, $\acute{a}$ is a patient parameter representing power of the tracheal respiratory sound signals and $\acute{b}$ is a patient parameter representing variations in tracheal anatomy producing the tracheal respiratory sound signals derived through a calibration process for each of the patient, $\overline{E}$ is an average of the tracheal sound energy, and $E_{base}$ is tracheal sound energy in the breath cycle used for calibration, calculating an entropy of the filtered tracheal respiratory sound signals defined according to the following:

$$H(p) = -\Sigma_{i=1}^{n} p_i \log p_i$$

wherein H is a probability distribution function of a sleep event, p is a probability distribution function of a tracheal sound amplitude defined by n bins with each bin spanning a range value from a minimum tracheal sound amplitude to a maximum tracheal sound amplitude, $p_i$ is a number of tracheal sound samples with a value equal to the $i^{th}$ bins divided by a total number of tracheal sound samples in the sleep event; and detecting by the processing module, using the estimated respiratory airflow rate and the entropy, sleep apneas and hypopneas; and reporting by the processing module the estimated respiratory flow rate and the sleep apneas and the hypopneas; and displaying on a display one or more plots from said reporting step.

15. The method according to claim 14 further comprising: collecting lung sound signals of the patient by a microphone.

16. The method according to claim 14 further comprising: extracting heart sounds from the tracheal respiratory sound signals of the patient by the processing module.

17. The method according to claim 14 wherein the sleep apneas is defined as a reduction of more than 90% in an amplitude of the respiratory airflow rate from a baseline followed by a decrease in the $SaO_2$ signals and the hypopneas is defined as a reduction of more than 50% in an amplitude of the respiratory airflow rate from a baseline followed by decrease in an amplitude of the $SaO_2$ signals ≥3%.

* * * * *